United States Patent
Horner et al.

(10) Patent No.: US 6,734,696 B2
(45) Date of Patent: May 11, 2004

(54) NON-CONTACT HYSTERESIS MEASUREMENTS OF INSULATING FILMS

(75) Inventors: Gregory S. Horner, Santa Clara, CA (US); Thomas G. Miller, Sunnyvale, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 0 days.

(21) Appl. No.: 10/286,358

(22) Filed: Nov. 1, 2002

(65) Prior Publication Data

US 2003/0117155 A1 Jun. 26, 2003

Related U.S. Application Data

(60) Provisional application No. 60/335,481, filed on Nov. 1, 2001.

(51) Int. Cl.$^7$ ............................................. G01R 31/02
(52) U.S. Cl. ................................. 324/765; 324/158.1
(58) Field of Search ................................. 324/765, 754, 324/750, 751, 752, 501, 537, 753, 158.1; 250/492.2; 438/14, 17, 18

(56) References Cited

U.S. PATENT DOCUMENTS

| | | | |
|---|---|---|---|
| 4,599,558 A | | 7/1986 | Castellano, Jr. et al. |
| 4,812,756 A | * | 3/1989 | Curtis et al. ................. 324/750 |
| 5,485,091 A | | 1/1996 | Verkuil |
| 5,498,974 A | * | 3/1996 | Verkuil et al. .............. 324/767 |
| 5,594,247 A | | 1/1997 | Verkuil et al. |
| 5,644,223 A | | 7/1997 | Verkuil |
| 5,650,731 A | | 7/1997 | Fung et al. |
| 5,767,691 A | * | 6/1998 | Verkuil ........................ 324/761 |
| 5,767,693 A | | 6/1998 | Verkuil |
| 5,834,941 A | | 11/1998 | Verkuil |
| 6,060,709 A | | 5/2000 | Verkuil et al. |
| 6,072,320 A | | 6/2000 | Verkuil |
| 6,091,257 A | | 7/2000 | Verkuil et al. |
| 6,097,196 A | * | 8/2000 | Verkuil et al. .............. 324/750 |
| 6,104,206 A | | 8/2000 | Verkuil |
| 6,121,783 A | | 9/2000 | Horner et al. |
| 6,191,605 B1 | | 2/2001 | Miller et al. |
| 6,202,029 B1 | * | 3/2001 | Verkuil et al. ................. 702/64 |
| 6,335,630 B2 | * | 1/2002 | Miller et al. ................. 324/767 |
| 2002/0090746 A1 | | 7/2002 | Xu et al. |

* cited by examiner

*Primary Examiner*—Kamand Cuneo
*Assistant Examiner*—Jimmy Nguyen
(74) *Attorney, Agent, or Firm*—Ann Marie Mewherter; Conley Rose P.C.

(57) ABSTRACT

Non-contact methods for determining a property of an insulating film are provided. One method includes measuring an amount of hysteresis in the insulating film without contacting the insulating film. The method also includes determining the amount of hysteresis in the insulating film. Computer-implemented methods for data analysis are also provided. One computer-implemented method includes determining a single numeric value representing an amount of hysteresis in an insulating film from electrical characteristics of the insulating film. The electrical characteristics are measured without contacting the insulating film. In addition, systems that include a measurement system and a computer-usable carrier medium are provided. The measurement system is configured to measure an amount of hysteresis in an insulating film without contacting the insulating film. The carrier medium includes program instructions, which are executable on a computer system for determining the amount of hysteresis in the insulating film using measurements from the measurement system.

21 Claims, 6 Drawing Sheets

NON-CONTACT HYSTERESIS MEASUREMENTS OF INSULATING FILMS

PRIORITY CLAIM

This application claims priority to U.S. Provisional Application No. 60/335,481 entitled "Non-Contact Hysteresis Measurements of Insulating Films," filed Nov. 1, 2001.

BACKGROUND OF THE INVENTION

1. Field of the Invention

This invention generally relates to methods for determining one or more properties of an insulating film. Certain embodiments relate to methods for determining hysteresis of an insulating film without contacting the insulating film.

2. Description of the Related Art

Fabricating semiconductor devices such as logic and memory devices may typically include processing a substrate such as a semiconductor wafer using a number of semiconductor fabrication processes to form various features and multiple levels of the semiconductor devices. For example, insulating (or dielectric) films may be formed on multiple levels of a substrate using deposition processes such as chemical vapor deposition ("CVD"), physical vapor deposition ("PVD"), and atomic layer deposition ("ALD"). In addition, insulating films may be formed on multiple levels of a substrate using a thermal growth process. For example, a layer of silicon dioxide may be thermally grown on a substrate by heating the substrate to a temperature of greater than about 700° C. in an oxidizing ambient such as $O_2$ or $H_2O$. Such insulating films may electrically isolate conductive structures of a semiconductor device formed on the substrate.

Measuring and controlling such insulating films may be an important aspect of semiconductor device manufacturing. A number of techniques are presently available for measuring hysteresis of insulating films. For example, electrical measurement techniques that rely on physical contact to a conductive electrode on top of an insulating film are able to determine hysteresis properties of insulating films using capacitance vs. voltage (C-V) and current vs. voltage (I-V) measurements. Such measurements have a long history and established utility.

Examples of physically contacting techniques that can be used to extract hysteresis measurements include depositing or growing the insulating film under test on a semiconducting or metallic substrate. In a first example, an electrode is deposited on top of the film under test, and the area of the electrode defines the area of measurement. A metal probe is placed in contact with a metal or polysilicon electrode, and an electrical bias is applied through the probe. In another example, a temporary electrode is lowered until it is in contact with the film under test. The electrode may be a conducting liquid (e.g., mercury), a conducting polymer, or any material that exhibits sufficiently conductive behavior. The area of the temporary electrode defines the area of measurement. An electrical bias is applied through the temporary electrode.

However, these measurements require a conductive electrode and a contacting probe. The necessity of direct physical electrical contact is particularly undesirable in many manufacturing situations. Accordingly, it would be advantageous to develop a method for measuring hysteresis without direct physical electrical contact.

SUMMARY OF THE INVENTION

An embodiment of the invention relates to a non-contact method for determining a property of an insulating film. The method includes measuring an amount of hysteresis in the insulating film without contacting the insulating film. The method also includes determining the amount of hysteresis in the insulating film. In one embodiment, the method may further include monitoring a presence of voids in the insulating film using the amount of hysteresis. The amount of hysteresis in the insulating film may be responsive to the presence of voids in the insulating film. In one such embodiment, the insulating film may be a low-k insulating film. In another such embodiment, the insulating film may be a high-k insulating film. In an additional embodiment, the method may include monitoring a presence of traps in the insulating film using the amount of hysteresis. The amount of hysteresis in the insulating film may be responsive to the presence of traps in the insulating film. In one such embodiment, the insulating film may be a thermally grown film. In another such embodiment, the insulating film may be a high-k insulating film. In a further embodiment, the method may include monitoring a presence of voids in the insulating film and a presence of traps in the insulating film using the amount of hysteresis.

In another embodiment, the insulating film may include a thermally grown film. In such an embodiment, the method may include processing the thermally grown film prior to measuring the amount of hysteresis. Therefore, the amount of hysteresis may be responsive to traps in the thermally grown film that may have been caused by the processing. In one embodiment, the method may also include processing the insulating film after formation of the insulating film and prior to measuring the amount of hysteresis. In this embodiment, the amount of hysteresis may be responsive to damage of the insulating film caused by the processing. In one example, the processing may include a plasma process.

In some embodiments, measuring the amount of hysteresis may include measuring an electrical characteristic of the insulating film before and after applying an electrical field to the insulating film. The electrical field may be applied for a period of time. In other embodiments, measuring the amount of hysteresis in the insulating film may include stressing the insulating film by applying an electrical field to the insulating field, by heating the insulating film, or by applying ultraviolet light to the insulating film. In one such embodiment, measuring the amount of hysteresis may also include measuring an electrical characteristic of the insulating film before and after stressing of the insulating film.

In one embodiment, the method may further include measuring one or more other properties of the insulating film. In addition, the method may include determining the one of more other properties of the insulating film from the measurements. In another embodiment, the insulating film may include an oxide. In such an embodiment, the method may include measuring trace metals in the oxide and determining an amount of the trace metals in the oxide. The method may include additional steps as described herein.

Another embodiment relates to a computer-implemented method for data analysis. The method includes determining a single numeric value representing an amount of hysteresis in an insulating film from electrical characteristics of the insulating film. The electrical characteristics are measured without contacting the insulating film. In one embodiment, the electrical characteristics of the insulating film are measured before and after application of an electrical field to the insulating film. The electrical field is applied to the insulating film without contacting the insulating film. In another embodiment, the method may include analyzing a bulk charge trap density in the insulating film using the single numeric value determined above. In an additional embodiment, the method may include analyzing polarization effects of voids in the insulating film using the single numeric value determined above. In a further embodiment, the method may include analyzing damage of the insulating film using the single numeric value representing the amount of hysteresis in the insulating film. In one such embodiment, the damage may be caused by processing of the insulating film performed after formation of the insulating film. The method may include additional steps as described herein.

An additional embodiment relates to a system that includes a measurement system and a computer-usable carrier medium. The measurement system is configured to measure an amount of hysteresis in an insulating film without contacting the insulating film. The carrier medium includes program instructions. The program instructions are executable on a computer system for determining the amount of hysteresis in the insulating film using measurements from the measurement system. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
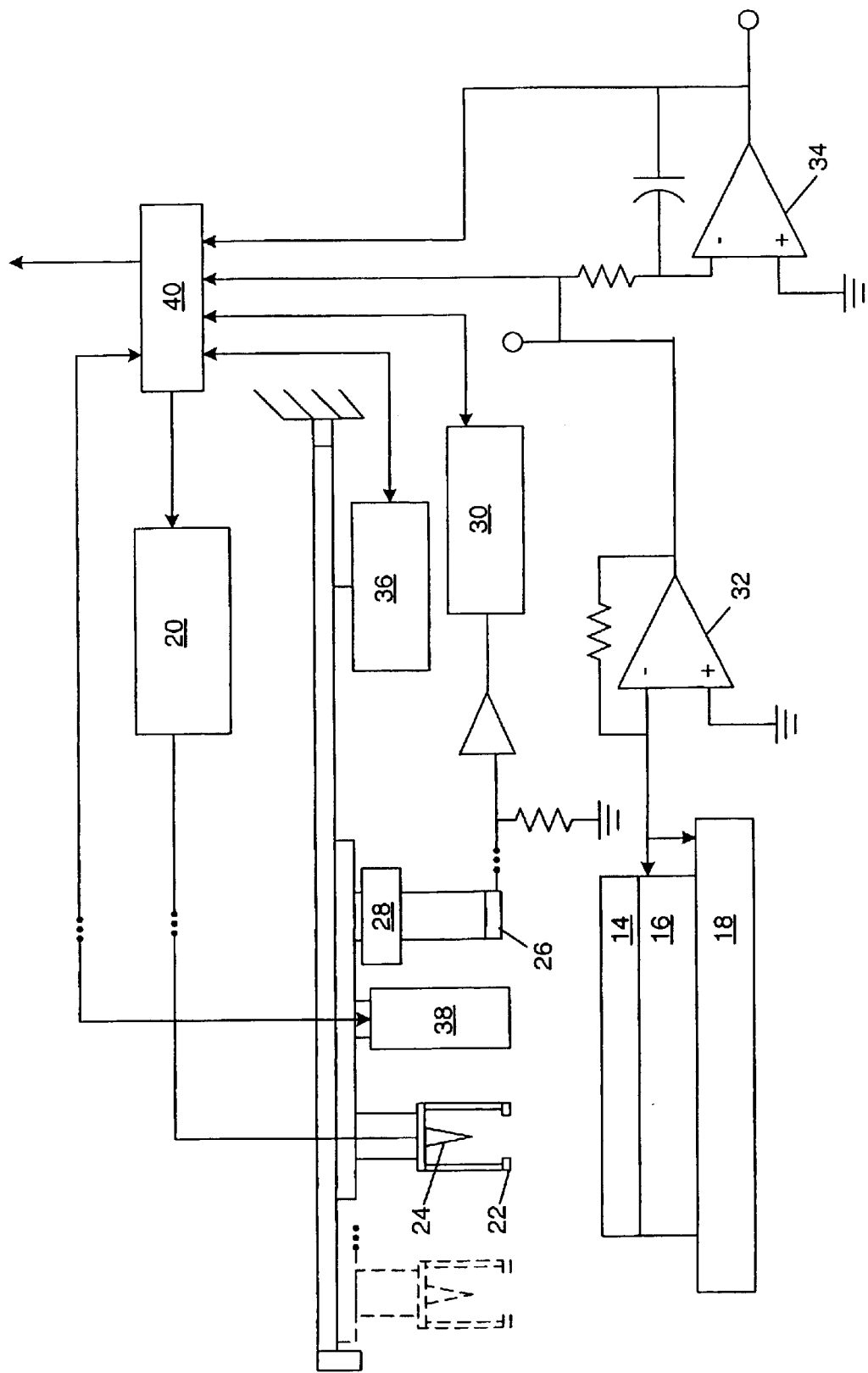
FIG. 1 is a schematic diagram of a side view of an embodiment of a system configured to measure electrical characteristics of an insulating film using non-contacting techniques.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following description generally relates to methods and systems for measuring electrical and physical properties of insulating films without contacting the insulating films. For example, the methods and systems described herein may be used to measure electrical hysteresis properties of or effects in insulating films in a non-contact manner. Such films may also be commonly referred to as "thin") insulating films. In general, hysteresis may be measured by applying an electrical field across the insulating film and measuring the resultant insulating film potential via non-contact electrostatic voltage and surface photovoltage measurements. Either charge trapping or polarization of voids in an insulating film may cause the hysteresis effects. Therefore, the methods and systems described herein may be used to measure insulating films in a non-contact manner and to determine the bulk charge trap density and/or polarization effects of voids within the insulating film.

Present technology for manufacturing integrated circuits and semiconductor devices makes extensive use of the formation of insulating films. These films may also be referred to as "dielectric layers." In a typical implementation, such an insulating film may include silicon dioxide ("$SiO_2$"), silicon nitride ("$Si_3N_4$"), or a nitrided form of amorphous $SiO_2$, which may be commonly referred to as oxynitride ("$SiO_xN_y$"). Many other materials are also commonly used. Such films may include materials commonly known as "low-k" or "high-k" insulating films, where "k" refers to the real part of the dielectric constant as measured at electrical frequencies. A low-k insulating film may include any material having a dielectric constant lower than about 3.9. Such low-k insulating films are generally used when reduced film capacitance per unit area is desired. Examples of commercially available low-k dielectric materials include, but are not limited to, proprietary materials known as Silc™, Black Diamond™, and Flare™. A high-k insulating film may include any material having a dielectric constant of greater than about 7. A high-k insulating film is often used when increased film capacitance per unit area is required for device operation. Examples of high-k materials include, but are not limited to, tantalum pentoxide ("$Ta_2O_5$"), hafnium dioxide ("$HfO_2$"), aluminum trioxide ("$Al_2O_3$"), and zirconium dioxide ("$ZrO_2$"). A low-k dielectric material may include any material having a dielectric constant of less than about 3.9. It is to be understood that the methodology described herein is not specific to any composition or thickness of insulating film being used.

In a typical application, the insulating films to be measured are on the upper surface of a substrate. Such insulating films may be formed, for example, by deposition or thermal growth on a conductive or semiconductor substrate. The substrate may include, but is not limited to, silicon, epitaxial silicon, silicon-on-insulator ("SOI"), or another semiconductor or conductive material such as gallium arsenide or indium phosphide. The substrate may also include any substrate commonly found and/or processed in semiconductor fabrication facilities, which may be commonly referred to as a "wafer." In other cases, the insulating film of interest may be the top layer of a stack of insulators, insulators and conductors, or conductors. In addition, a conductor may also be formed on an upper surface of the insulating film.

The control and measurement of insulating (or dielectric) films is an important aspect of integrated circuit manufacturing. Hysteretic behavior in insulating films is not desired due to its negative impact on semiconductor device stability. However, hysteretic behavior is known to exist in relatively low-quality insulating films. For example, hysteretic behavior may exist in thermally grown films (i.e., $SiO_2$), which are produced in furnace conditions that may allow the formation of relatively large densities of bulk oxide traps. In another example, hysteretic behavior may exist in thermally grown films (i.e., $SiO_2$) that are grown with an initially low density of bulk oxide traps, but which are damaged during subsequent processing. For example, a thermally grown film may be damaged during plasma processing of the insulating film. Examples of such plasma processing include, but are not limited to, plasma assisted etching, plasma assisted oxide deposition, and photoresist ashing. In addition, insulating films (either deposited or thermally grown) that exhibit void formation in the bulk of the insulating film may also exhibit hysteretic behavior. Examples of such insulating films include new generations of low-k insulating films, which benefit from the presence of voids to lower the average dielectric constant, but which may suffer from the effects of electrical hysteresis. A second example is high-k insulating films, which are intended to be substantially continuous and substantially void-free, but which may suffer from void formation and high bulk trap densities that allow bulk charge trapping.

Regardless of the dielectric constant of insulating films, all insulating films may exhibit hysteretic behavior due to three basic film properties. For example, when an electrical field is applied across an insulating film, electrical current may flow through the film due to defect-assisted conduction, thermally-assisted transport, or quantum mechanical tunneling. In general, the electrical current increases with field strength. Various theoretical models describing mechanisms for current transport through relatively thin insulating films have been developed and published. Examples of such models include, but are not limited to, Fowler-Nordheim tunneling, direct tunneling, Poole-Frenkel conduction, hopping conduction, space charge limited conduction, and Shottky or Thermionic conduction. Such theoretical models may have a general form of $I=f(V, \text{physical}\_T_{film}, \text{other}\_\text{material}\_\text{parameters})$. For example, the Fowler-Nordheim tunneling model has the following form:

$$I = A_1(V/T_{film})^2 \exp(A_2 * T_{film}/V). \tag{1}$$

Other models of leakage have different functional dependencies. In general, all such models may be expressed in a functional form such as:

$$I = \text{function}(T_{film}, V, A_1, A_2, \ldots A_N), \tag{2}$$

where $A_1, A_2 \ldots A_N$ represent constants that may or may not be of interest. The dominant current mechanism for a given film depends on the thickness, chemical composition, and nature of film defects, but in all cases the current flow may produce two hysteresis-related instabilities.

Some hysteresis effects are related to slow charge trapping within insulating films. For example, all insulating films (whether deposited or thermally grown) may contain bulk defects. When the bulk defect density of an insulating film exceeds a certain threshold (i.e., about 1E10 defects/$cm^2$, for applications in semiconductor device manufacturing), charge trapping at the bulk defects may have measurable effects on film performance and stability.

As an illustration, consider an insulating film disposed between a metal plate and a moderately doped silicon substrate. The film contains one defect state. This defect state is located proximate the center of the film (i.e., about half way between the metal plate and the silicon substrate). The defect is able to capture electrons that travel through the film with a probability per unit time, P1. When an electron is captured, it remains in the trap for an average time, T1.

First, assume that the trap is empty (i.e., no electrons have been trapped in the film), and a field is applied across the film. The field is varied in a stepwise fashion while measuring the film capacitance, to determine the flatband voltage of the film in a conventional manner. The measured flatband voltage is directly influenced by the amount of charge trapped in the film. The result, for this hypothetical film, is $V_{fb\_no\_trap}=0.0$ V. Although a current flowed through the film when the electrical field was applied, there was insufficient probability of electron capture. Therefore, the film defect remains unoccupied. A positive electrical field is then applied to the film for a sustained amount of time, T2(T2>>1/P1). An electron is trapped, and it resides in the trap for a time, T1.

The sustained electrical field is terminated, and a second electrical field sweep is initiated to once again measure the flatband voltage. With the trap now occupied (and the elapsed time since trap occupation <T1), a new flatband voltage is measured. For example, $V_{fb\_trap}=0.1$ V. The shift in flatband voltage may be determined using the following equation:

$$V_{shift} = V_{fb\_trap} - V_{fb\_no\_trap} = 0.1 \text{ V}. \tag{3}$$

The effective trapped charge density may be determined using equation 4:

$$Q_{eff\_trapped} = C_{film} * (V_{shift}) \tag{4}$$

where $C_{film}$ is the film capacitance per unit area (commonly reported in Farads/$cm^2$). This shift in the C-V or I-V characteristics of the film is commonly referred to as "hysteresis" and provides a measure of the charge trap density of the film.

One signature of slow charge trapping is that the flatband voltage (or midband voltage, threshold voltage, or other characteristic film voltages) becomes more positive after the application of a positive electrical field. Another signature of slow charge trapping is that the flatband voltage (or midband voltage, threshold voltage, or other characteristic film voltages) becomes more negative after the application of a negative electrical field.

Other hysteresis effects are related to film polarization. For example, a second hysteresis effect may be measured when voids (or other electrically polarizable domains) are present in the insulating film. The presence of voids is most often associated with low-k films, but all films may suffer from the presence of voids to a certain extent. In the case of low-k films, measuring the hysteresis due to film polarization provides a means of monitoring the percent fraction of voids, which is an important control parameter in semiconductor low-k film manufacturing. The hysteresis of film polarization is distinguishable from slow bulk charge trapping, as illustrated in the following example.

Consider a film disposed between a metal plate and a moderately doped silicon substrate. The film contains one void (or other electrically polarizable domain), and dangling bonds populate the inner surface of the void. The dangling bonds exhibit no net charge, and electrons and holes randomly populate the bonds. Thus, the net polarization vector of the void is zero. The void exhibits an ability to develop a polarization vector by redistributing charge along the dangling bonds in a non-random fashion when an electrical field is applied. Relaxation to or from a non-polarized state takes a time, T1.

First, assume that the void has a net polarization vector of zero. Apply a field across the oxide, and vary this field in a stepwise fashion while measuring the film capacitance, to determine the flatband voltage of the film in a conventional manner (measurement time<<T1). The measured flatband voltage is directly influenced by the amount of charge trapped in the film (in this case zero) and additional potentials (such as those due to void polarization) that may develop within the film. The result, for this hypothetical film, is $V_{fb\_no\_polarization}=0.0$ V. We now apply a positive electrical field to the film for a sustained amount of time, T2 (T2>>T1). The void develops a net polarization vector during this time.

The sustained electrical field is terminated, and a second electrical field sweep is initiated to once again measure the flatband voltage. With the void now polarized (and the elapsed time since polarization<T1), a new flatband voltage is measured. For example, $V_{fb\_trap}=-0.1$ V. The shift in flatband voltage may be determined using the following equation:

$$V_{shift}=V_{fb\_trap}-V_{fb\_no\_trap}=-0.1\ V. \quad (5)$$

This shift in the C-V or I-V characteristics of the film is generally referred to as "hysteresis" and provides a measure of the void density or electrical polarizability of the film.

One signature of film polarization is that the flatband voltage (or midband voltage, threshold voltage, or other characteristic film voltages) becomes more negative after the application of a positive electrical field. Another signature of film polarization is that the flatband voltage (or midband voltage, threshold voltage, or other characteristic film voltages) becomes more positive after the application of a negative electrical field.

A third hysteresis mechanism is related to film damage. As an illustration, consider an insulating film that has no initial polarization and a charge trap density of about 0. Measure the initial flatband voltage (as before, $V_{fb\_initial}=0.0$ V). Next, apply a high positive field to the film. As a current begins to flow through the film, energetic electrons cause damage in the film, and create oxide defect states by breaking the bond structure of the film. A fraction of the newly created states may become populated with electrons. A second electrical field sweep is initiated to once again measure the flatband voltage. In this case, the second flatband voltage may differ significantly from the initial flatband voltage due to the change in oxide charge density. This shift is distinguished from the example provided above with respect to hysteresis due to slow charge trapping, because the trap states did not exist prior to the measurement. In the example of hysteresis due to slow charge trapping, the states existed prior to measurement, but were simply not populated with electrons.

The methods and systems described herein apply to determining insulating film hysteresis using, specifically, non-contact techniques. In one example, the field is applied by spraying a controlled burst of corona (i.e., ionized air) at the surface of the film. The charges adhere to the surface of the film and creates an electrical field across the film. Placing known amounts of either positive or negative corona on the surface of the film controls the strength and polarity of the field. In a second example, a probe is brought close to (but not in contact with) the surface of the film. In this case, an electrical field is applied to the film by forcing the probe to a known potential. The potential drop is divided across the combined series of airgap and film capacitances. In either case, the flatband voltage (or I-V, or other electrical characteristics such as threshold voltage, midband voltage) is measured before and after application of the electrical field to the insulating film. The change in flatband voltage (or other film characteristic) is used to calculate either the charge trapping, the film polarization, or a combination of charge trapping and film polarization.

If the insulating film does not include a single layer, but includes a plurality of layers of insulators and/or conductors, then the methods described herein can still be followed. In such instances, a lump sum effective charge trapping and polarization will be reported. The presence of a conductive layer on top of the insulating film also presents no significant hindrance to the non-contact methods and systems described herein, as long as the charge deposition is known to be constrained to an area, A. Such a charge constraint may be achieved by forming a pattern upon or within such an upper conductive layer using any method known in the art.

An example of a measurement system configured to measure an electrical characteristic of an insulating film using non-contacting techniques is illustrated in FIG. 1. The system may be configured to measure current-voltage characteristics of insulating film 14 formed on substrate 16. Insulating film 14 may include any of the insulating films described above such as an oxide. In addition, substrate 16 may include any of the substrates described above such as a semiconductor wafer. The system may include wafer chuck 18 configured to hold substrate 16 during a measurement process. Wafer chuck 18 may also provide a grounding contact to substrate 16. The grounding contact may be obtained, for example, from a high pressure contact using a sharp tungsten carbide needle. The system may also include high voltage supply 20 coupled to corona gun 22. High voltage supply 20 may be configured to supply high voltage (i.e., about 6 kV to about 12 kV) to the corona gun to produce positive or negative corona charges depending on the polarity of supply 20. Corona gun 22 may include one or more needles 24 coupled to high voltage supply 20.

In addition, the system may include Kelvin probe 26. Kelvin probe 26 may include an electrode coupled to vibrator 28. Movement of probe 26 above a charged surface may result in an AC voltage representative of the potential of the charged surface. Kelvin controller 30 may be configured to convert an AC voltage to a signal corresponding to the voltage of the surface.

Current flowing through insulating film 14 and substrate 16 from corona gun 22 may be converted to a voltage by the current-to-voltage converter 32. This voltage (current) may be integrated by charge integrator 34 to provide a measure of the charge deposited by corona gun 22 on insulating film 14. The circuits, thus, are configured as a coulombmeter. The system may also include position actuator 36. Position actuator 36 may be configured to move corona gun 22 and Kelvin probe 26 over substrate 16, as shown in phantom in FIG. 1. The system may also include surface photo voltage (SPV) device 38. SPV device 38 may be configured to make an SPV measurement of the insulating film using a relatively high intensity light source such as a xenon flash tube.

The system may further include controller 40 configured to control operation of the system. Controller 40 may be configured to control position actuator 36 and high voltage supply 20 in response to Kelvin controller 30, current-to-voltage converter 32, and current integrator 34. The controller may also be configured to provide a measurement of the current-voltage behavior of insulating film 14 and substrate 16. The controller may be, for example, a dedicated microprocessor-based controller or a general purpose computer. The controller may be further configured as described herein.

For ease of understanding, an example of a measurement of the I-V characteristics of a thermal oxide on a P-silicon substrate with a negative polarity corona, which is illustrated in U.S. Pat. No. 6,097,196 to Verkuil et al. is incorporated below with reference to the system illustrated in FIG. 1. Although the example illustrated by Verkuil et al. is described with respect to a thermal oxide on a silicon substrate, it should be understood that the measurement described herein is applicable to a variety of insulating or dielectric films grown and/or deposited on a variety substrates of semiconductor materials or metals. The charge used can be positive or negative, as appropriate.

The oxide current, $I_{ox}$ may be expressed as the product of the oxide capacitance per unit area, $C_{ox}$, and the derivative with respect to time of the voltage across the oxide, ($dV_{ox}/dt$). $C_{ox}$ can be calculated from $E_0 \cdot E_{ox}/T_{ox}$, where $E_0$ is the permittivity of free space (8.86E-14 farads/cm), $E_{ox}$ is the relative dielectric constant of the oxide (3.9 for thermal oxide), and $T_{ox}$ is the thickness of the oxide in cm. The derivative of $V_{ox}$ can be approximated by the change in $V_{ox}$, $\Delta V_{ox}$, during a time $\Delta t$ in s.

An increment of charge as determined by current integrator 34 is deposited on the oxide surface by corona gun 22, and the voltage $V_{ox}$ is measured by Kelvin probe 26. After a delay, $\Delta t$, $V_{ox}$ is measured again. These measurements can be used to determine a value for $dV_{ox}/dt$, which is used to determine $I_{ox}$. This change in voltage results from the reduction of charge over the interval $\Delta t$. The time $\Delta t$ that is used varies with the oxide thickness and is selected to provide the desired sensitivity for measuring the oxide current. The increments of charge can also be summed to provide the cumulative deposited charge, $Q_{ox}$.

In general, it may also be necessary to remove any undesired charge from the surface of the insulating film before starting the measurements. For example, the voltage may be measured with Kelvin probe 26 and the charge may be applied with corona gun 22 until the oxide voltage is at a relatively low value (e.g., −2 V for a 1,000 Åoxide) corresponding to a low field and a slight degree of silicon accumulation. As a first approximation, the voltage reading of the Kelvin probe, $V_{KP}$, will be equal to $V_{ox}$. This approximation will hold very well for thick oxides (e.g., greater than 2,000 Å), where the work function difference, $V_{WF}$, between the Kelvin probe and the silicon bulk can sometimes be ignored and where the silicon surface potential, $V_{si}$, (which is in series with $V_{KP}$) can also sometimes be ignored.

In order to estimate the actual value of the oxide voltage, $V_{ox}$, $V_{KP}$ must be corrected for the fact that $V_{KP}=V_{ox}+V_{WF}+V_{si}$. Therefore, $V_{WF}$ and $V_{si}$ are first estimated and subtracted from $V_{KP}$. $V_{WF}$ can be estimated by first substituting a material, with a predetermined, known work function, such as gold or graphite, in place of the wafer and then measuring $V_{KP}$.

$V_{si}$ can be estimated from a SPV measurement using a very high light intensity source such as xenon flash. Devices for making SPV measurements are well-known in the art. For a given value of SPV and a reasonably estimated value of excess optically induced carrier generation, delta n, there will be an approximate corresponding value of $V_{si}$ that can be calculated from a theoretical model, such as that of E. O. Johnson, Phys. Rev., Vol. 111, No. 1. The first order effect in the Johnson model is that the magnitude of SPV tends to approach $V_{si}$, and delta n becomes comparable to and larger than the silicon doping concentration. It is noted that delta n can also be estimated from Johnson, based on a SPV measurement in strong accumulation and in strong inversion. For more accuracy and/or thinner oxides, the above corrections can be employed.

In the preferred embodiment, oxide 14 starts at zero volts, either inherently or by application of the appropriate polarity and quantity of corona charge by corona gun 22. A negative increment of corona charge $\Delta Q_c$ is deposited onto the oxide surface by corona gun 22. As a result, a first oxide voltage, $V_{OX1}$, is measured by Kelvin probe 26. After a pause, $\Delta t$, Kelvin probe 26 measures a second oxide voltage, $V_{OX2}$. The difference between the voltages is used with $\Delta t$ to determine $I_{OX}$. The incrementing of the corona charge $\Delta Q_c$ and the calculation of the resulting $I_{OX}$ continues until an I-V characteristic of interest has been generated.

Figure 2:
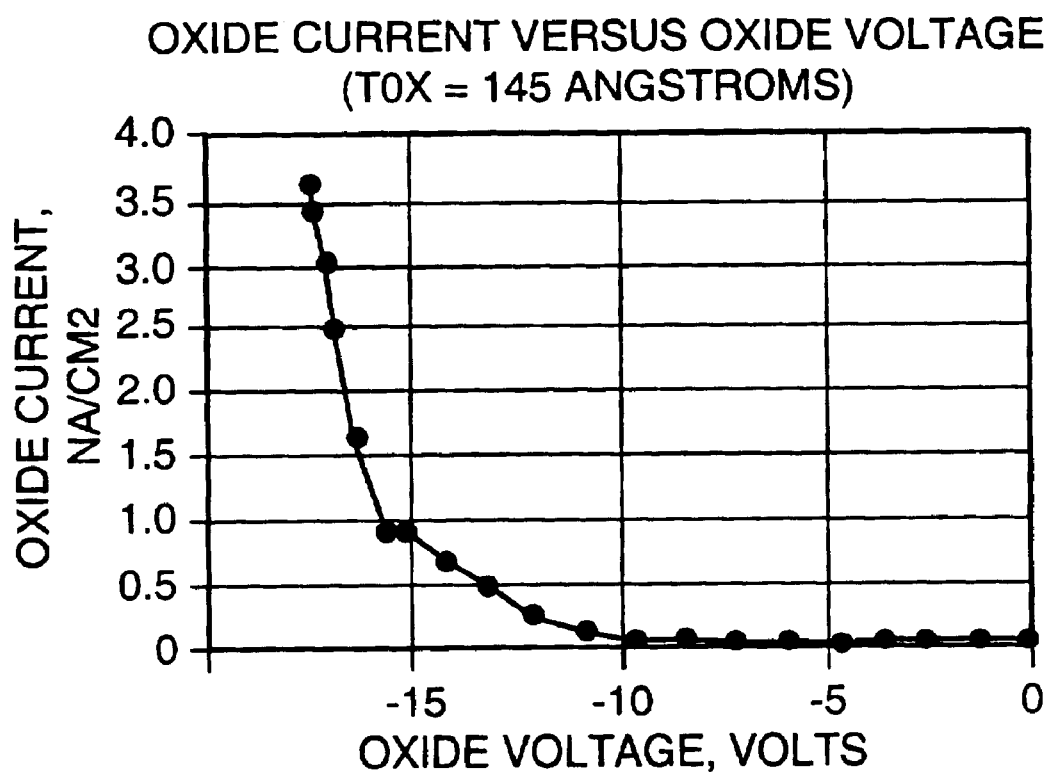
FIG. 2 is an exemplary graph of current versus voltage for a thin oxide under test.

Referring to FIG. 2, a graph of I-V results from the above method for a thermal oxide layer with a thickness of 143 Å is shown. The $\Delta t$ used was 15 seconds. The charge increment was about 3.3E-7 coulombs/cm$^2$.

Figure 3:
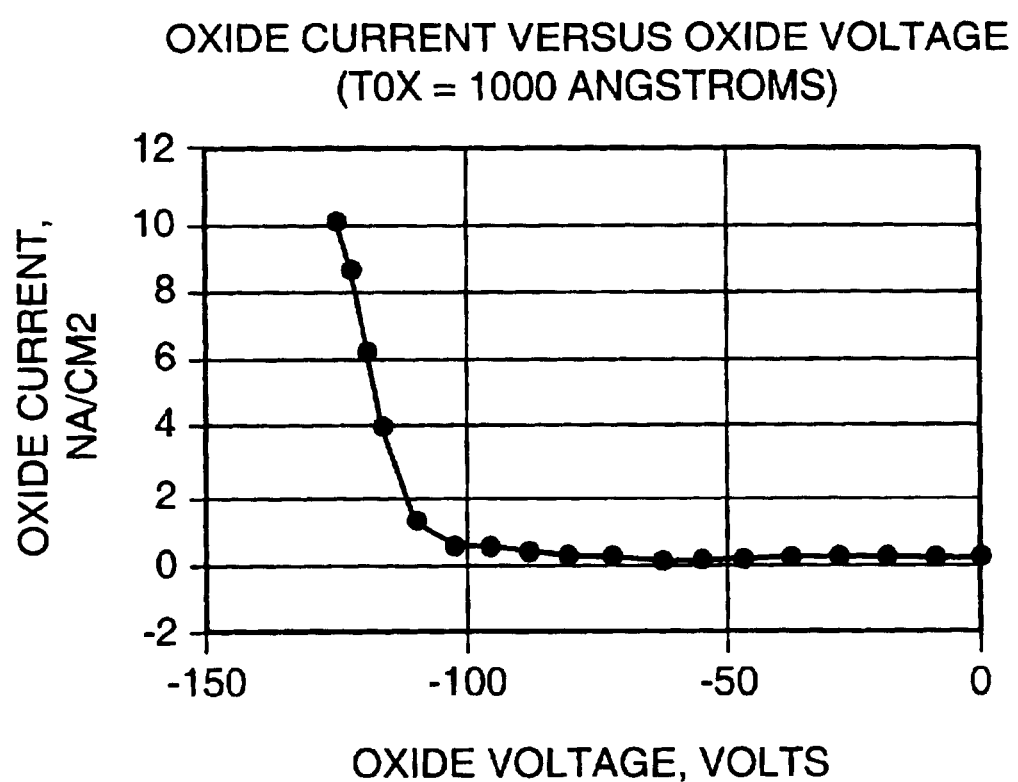
FIG. 3 is an exemplary graph of current versus voltage for a thick oxide under test.

Referring to FIG. 3, a graph of I-V results from the above method for a thermal oxide layer with a thickness of 1,000 Å is shown. The $\Delta t$ used was 60 seconds. The charge increment was about 3.3E-7 coulombs/cm$^2$.

The I-V graphs in FIGS. 2 and 3 can be used to identify the oxide voltage or electric field at a given conduction current. Conversely, FIGS. 2 and 3 can also be used to identify the conduction current corresponding to a given value of oxide voltage or field strength. In addition, the likely existence of a particular conduction mechanism of interest can be postulated by curve-fitting various oxide conduction models to the I-V behavior in FIGS. 2 and 3. For example, conduction due to tunneling behavior would tend to exhibit an I-V characteristic, $I=V_{OX}^2*\exp(-b/V_{OX})$, where b is a constant. This tunneling behavior occurs, for example, in thermal oxides. Conduction due to field enhanced thermal excitation of carriers from bulk oxide traps (known as Frenkel-Poole Emission) would tend to exhibit an I-V characteristic, $I=V*\exp(f(T,V))$, where $f(T,V)$ is a function of temperature and the voltage across the dielectric, V. Frenkel-Poole Emission is observed, for example, for silicon nitride layers.

The accuracy of the I-V characteristic can be further improved by correcting for $V_{WF}$ and $V_{si}$ (in case of substrates other than silicon, other surface potentials can be evaluated). One example of methods for increasing the accuracy of measurements of insulating films is illustrated in U.S. Patent Application Serial No. to Horner et al., entitled "Methods for Non-Contacting Differential Voltage Measurements," filed on Nov. 1, 2002, which is incorporated by reference as if fully set forth herein.

The work function of a material is defined as the energy required to remove an electron from the Fermi level, physically extract it from the material, and move it an infinite distance away from the material. $V_{WF}$ can be expressed as the work function difference between the work function of the Kelvin probe electrode, $W_{KP}$, and the work function of the silicon bulk, $W_{si}$, of the wafer under test. While $W_{si}$ is known to be about 4.8 eV, $W_{KP}$ is usually unknown and may drift due to dipole effects from adsorbed air molecules.

$W_{KP}$ can be determined by making a calibrating Kelvin probe measurement, $V_{KP2}$, of a material having a predetermined effective work function, $W_{REF}$, in place of wafer 16. For example, highly oriented pyrolytic graphite may be used as a reference material. This graphite has the advantage that a freshly cleaved surface can be obtained by applying and removing a piece of adhesive tape from the surface. This fresh surface allows for very repeatable measurements of $W_{KP}$, where $W_{KP}=V_{KP2}-W_{REF}$. It follows then that $V_{WF}=V_{KP2}+W_{REF}-W_{si}$. The resulting value for $V_{WF}$ is subtracted from $V_{KP}$ by controller 40 to provide a corrected value for $V_{OX}$.

SPV device 38 is used to make an SPV measurement using a very high intensity light source such as a xenon flash tube. The resulting value of the SPV measurement is then used to estimate $V_{si}$, which is then subtracted from $V_{KP}$ by controller 40 to provide a corrected value for $V_{OX}$.

The light intensity must be sufficient for creating a concentration of excess light induced carriers that is comparable to or greater than the doping concentration of the wafer (e.g., 1E15 carriers/cm$^3$). The excess carriers (electrons and holes) will separate in the silicon surface field, due to $V_{si}$ and then set up an opposing field that will tend to reduce $V_{si}$ toward zero. Therefore, the magnitude of the SPV (actually, the change in $V_{si}$) will tend to be a significant fraction of $V_{si}$. For silicon, in the depletion regime, the SPV can be as much as 80% of $V_{si}$. For the accumulation regime, the SPV will tend to be about 30% of $V_{si}$.

The need to correct for $V_{WF}$ and $V_{si}$ becomes greater for thinner oxides. An uncorrected error in $V_{WF}$ could be as high as 1 V. For a 2,000 Å oxide this could correspond to a tunneling field error of 0.05 Mv/cm, which would be a 0.6% error for a nominal tunneling field of about 8 Mv/cm. In contrast, for a 50 Å oxide, the error would go up to 25%. By correcting for $V_{WF}$, this latter error can be reduced to about 5%.

An uncorrected error in $V_{si}$ can also be significant. Assuming a true oxide conduction current of about 46E-9 amps/cm$^2$ for a 2,000 Å thick oxide, the theoretical drop in oxide voltage per second would be about 265 mv/sec. Without using $V_{WF}$ or $V_{si}$ correction results, for example, in a measured drop in oxide surface voltage of 283 mv/sec or a 7% error.

In the case of a 50 Å thick oxide, the theoretical drop in oxide voltage per second would be about 7 mv/sec. Without using $V_{WF}$ or $V_{si}$ correction results, for example, in a measured drop in oxide surface voltage of 30 mv/sec, or 400% error. Correcting the measurement for $V_{si}$ and $V_{WF}$ realistically reduces the error by a factor of ten.

The theoretical values are based on the Johnson Model, assuming that the excess light induced carrier concentration was a reasonable value equal to ten times the doping concentration of the wafer, which was assumed to be 1E15 atoms/cm$^3$.

Figure 4:
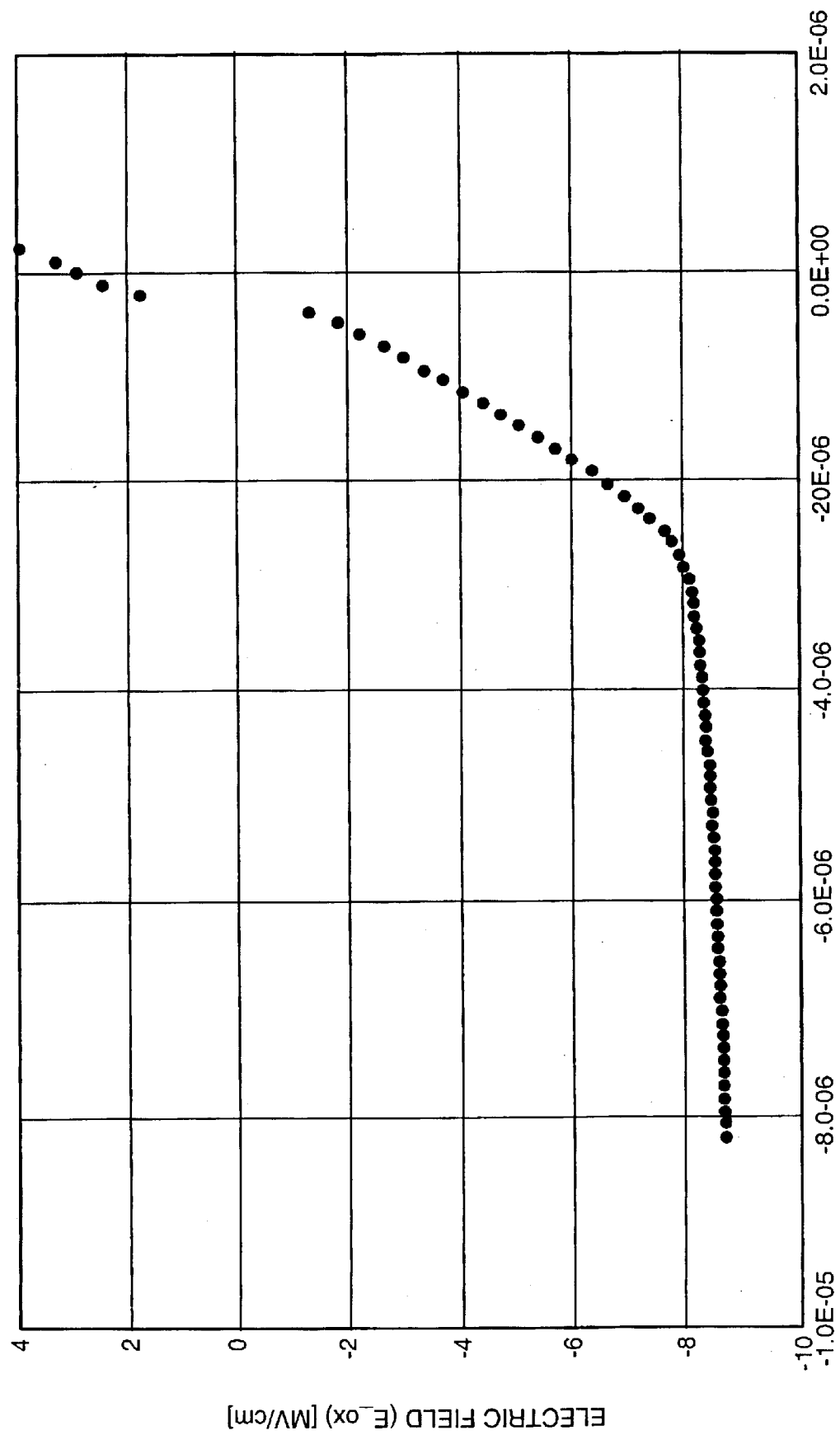
FIG. 4 is an exemplary graph of electrical field versus corona charge for a tunneling field test on an oxide.

The measured data can also be advantageously used to determine the tunneling field for an oxide. Referring to FIG. 4, electrical field strength ($V_{OX}/T_{OX}$) as a function of deposited corona charge, $Q_{OX}$ is shown. This is a convenient way of finding the saturating, terminal value of the oxide field corresponding to increasing deposited corona charge density. In FIG. 4, the electric field strength in a 28.8 Å thermal oxide approaches a terminal value as the oxide conduction current (coulombs/sec-cm$^2$) approaches the rate of corona deposition (coulombs/sec-cm$^2$) due to tunneling. This terminal value (here, about 8 Mv/cm) is referred to as the "tunneling field."

Tunneling field may also be measured more directly with the system. Corona gun 22 is used to deposit a charge on oxide 14 that would be sufficient to establish a field strength greater than the expected tunneling field (e.g., 7–10 Mv/cm). This predetermined value of excess charge only creates a field corresponding to the tunneling field due to the resulting tunneling current. The resulting $V_{OX}$ is measured with Kelvin probe 26 and the tunneling field determined from $V_{OX}/T_{OX}$. The repeatability and accuracy of the measurement can be improved by controlling the corona deposition rate, total corona charge, and elapsed time before making the $V_{OX}$ measurement.

The method allows measurement of I-V characteristics and tunneling field without spurious results due to localized defects such as pinholes. Because no conductor is applied to the surface of the dielectric, the localized defects stay localized as only the local corona charge is available to pass through the defect. It is also noted, that for tunneling current measurements, this method offers the added advantage of not having otherwise, undesirable, enhanced tunneling around the abrupt edge of a MOS electrode. This edge effect problem was discussed in T. B. Hook and T. P. Ma, J. Applied Physics. 59 (11), Jun. 1, 1986. For the Corona-Oxide-Semiconductor electrode used above, the charge density around the effective edge of the electrode will tend to be tapered, as opposed to a MOS electrode.

Hysteresis may be measured and may used to determine void fraction as described in more detail above.

Figure 5:
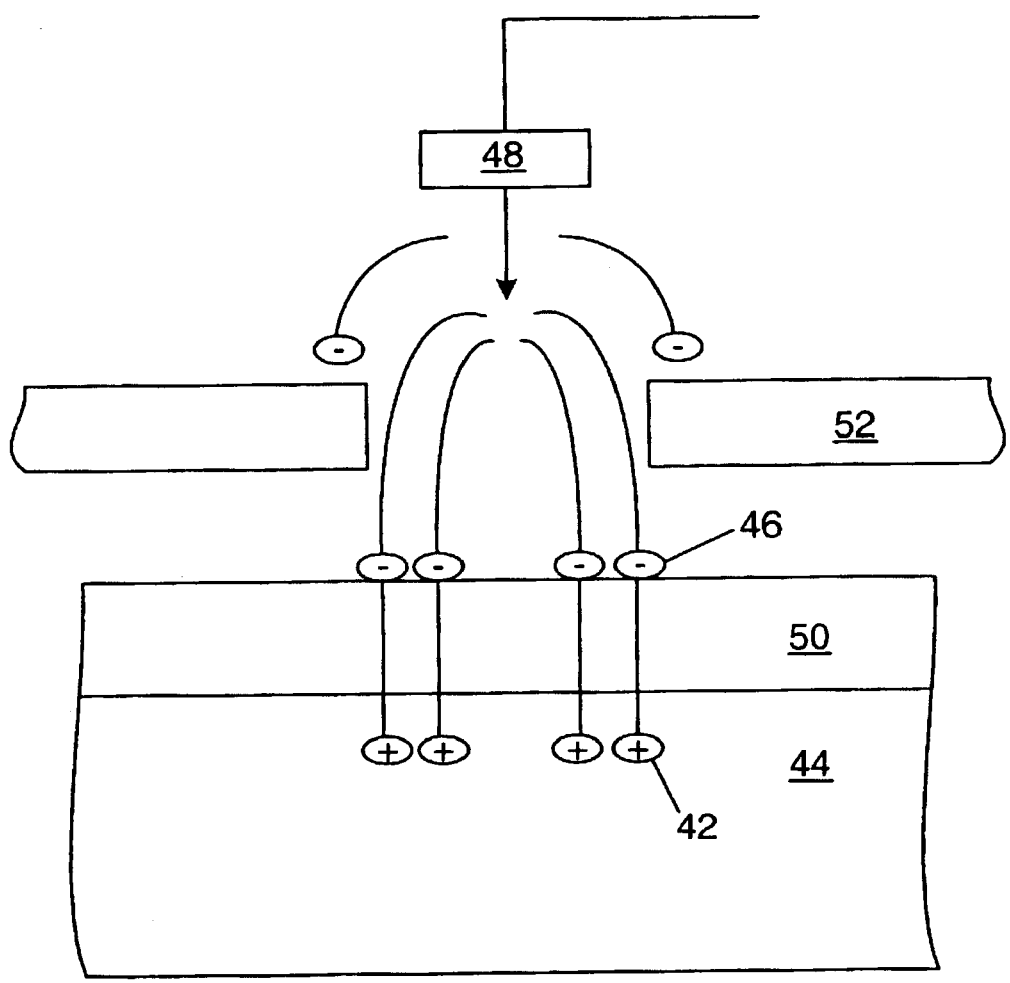
FIG. 5 is a schematic diagram of a side view of an embodiment of a charge deposition on a surface of an insulating film using a corona source.

FIG. 5 illustrates an embodiment of a charge deposition on a surface of an insulating film using a corona source. As shown in FIG. 5, positive charge accumulation 42 in p-type silicon substrate 44 may result from the deposition of negative charges 46 from negative corona source 48 onto surface of oxide layer 50 overlying substrate 44. The corona discharge may be applied to the area of interest via mask 52. In one embodiment, it may be necessary for purposes of obtaining accurate thickness measurements, that a uniform density of charge 46 be deposited through the aperture in mask 52.

Figure 6:
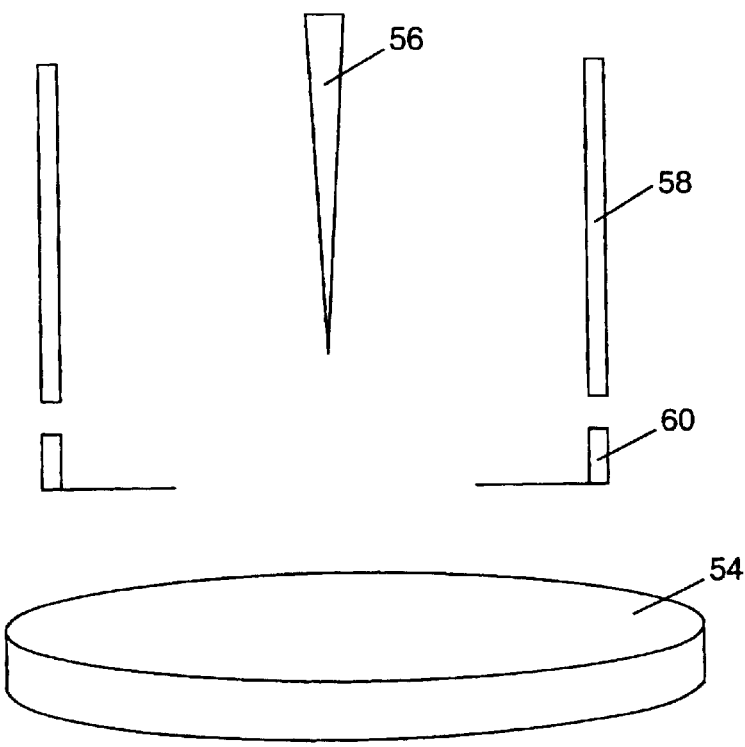
FIGS. 6 and 7 are schematic diagrams of partial cross-sectional views of alternative embodiments of a corona source.
Figure 7:
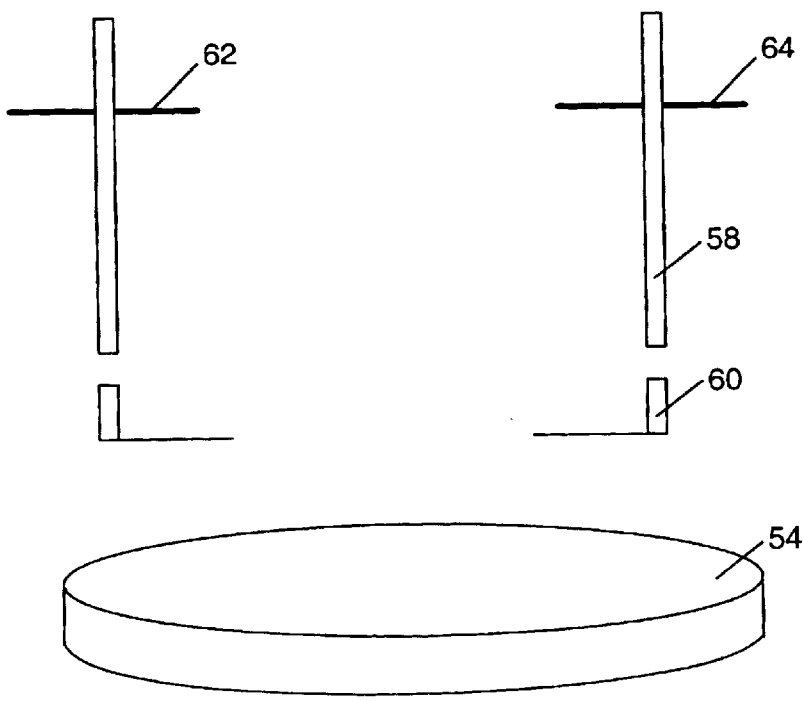

FIGS. 6 and 7 illustrate partial cross-sectional views of alternative embodiments of a corona source, which may be used to deposit a charge substantially uniformly over an area of specimen 54. Specimen 54 may include an insulating film and a substrate as described herein. The corona sources may be configured to provide a well-defined and substantial beam charge density (to minimize measurement time) having relative uniformity (for measurement accuracy) across the selected site of interest on specimen 54. As shown in FIG. 6, the corona source may include needle 56 and beam shaping electrodes 58 and 60. Beam shaping electrodes 58 and 60 may be arranged concentric with an axis of needle 56. Beam shaping electrodes 58 and 60 and the biasing voltages applied thereto may improve the corona charging capability of the gun in two important ways. First, lower electrode 60 may act as a mask for defining the diameter of the area of corona deposition. Second, the bias voltage on electrode 60 (same polarity as the corona ions) repels ions that normally would be captured by the edge of electrode 60 and directs them down to the specimen site with an enhanced density that abruptly ceases under the edge of electrode 60.

Upper electrode 58 may help to boost the efficiency of the corona source by being biased at a relatively high voltage (up to ±3 kV) with the same polarity as the corona ions. Potentials in the range of ±6–9 kV and up to ±1.5 kV are appropriate for needle 56 and mask electrode 60, respectively. This may result in an electrical field configuration, in the upper region of the corona source, that prevents many of the ions from being captured by the upper electrode and directs them down to lower electrode 60 which, in turn, directs them to the specimen site. It should be noted that needle 56 and electrodes 58 and 60 may be supported and insulated from each other by suitable insulated support members (not shown) that may allow for the application of the necessary biases.

FIG. 7 is essentially the same as FIG. 6 except for the important difference that two facing and horizontal needles 62 and 64 are provided in FIG. 7 in lieu of the single vertical needle 56 of FIG. 6. The potential applied to needles 62 and 64 and electrodes 58 and 60 of FIG. 6 may be the same as the corresponding parts in the case of FIG. 6.

Additional examples of non-contact corona sources are illustrated in U.S. Pat. Nos. 4,599,558 to Castellano et al., 5,594,247 to Verkuil et al., and 5,644,223 to Verkuil and are incorporated by reference as if fully set forth herein. In an embodiment, a system as described herein, may include a non-contact work function sensor such as a Monroe probe in place of a Kelvin probe. Further examples of work function sensors that may be incorporated into the system are illustrated in U.S. Pat. Nos. 4,812,756 to Curtis et al., 5,650,731 to Fung, and 5,767,693 to Verkuil, which are incorporated by reference as if fully set forth herein. In addition, any other appropriate system and corona source known in the art may be used for carrying out a method as described herein.

In one embodiment, the method may further include measuring one or more other properties of the insulating film. In addition, the method may include determining the one of more other properties of the insulating film from the measurements. In another embodiment, the insulating film may include an oxide. In such an embodiment, the method may include measuring trace metals in the oxide and determining an amount of the trace metals in the oxide. In an embodiment, metal contamination in insulating film may be detected by annealing the insulating film such that a portion of the metal contamination is driven into the insulating film. After the insulating film is annealed, an electrical characteristic of the insulating film may be measured. The electrical characteristic may include a surface voltage, a flatband voltage, an interface trap density, a total dielectric charge of the charged dielectric material, or a determined resistivity of the dielectric material. The measured electrical characteristic may be used to determine a characteristic of the metal contaminant. Characteristics may include determining the presence of metal contaminants, the identity of the metal contaminant, and the concentration of the metal contaminants, or all of the above. Such a method is further illustrated in U.S. patent application Ser. Publication No. 2002-0090746-A1 published on Jul. 11, 2002 by Xu et al., which is incorporated by reference as if fully set forth herein.

Another embodiment relates to a computer-implemented method for data analysis. The method includes determining a single numeric value representing an amount of hysteresis in an insulating film from electrical characteristics of the insulating film. The electrical characteristics are measured without contacting the insulating film as described above. The single numeric value representing the amount of hysteresis in the insulating film may be determined as described above. In another embodiment, the method may include analyzing a bulk charge trap density in the insulating film using the single numeric value as described above. In an additional embodiment, the method may include analyzing polarization effects of voids in the insulating film using the single numeric value as described above. In a further embodiment, the method may include analyzing damage of the insulating film using the single numeric value representing the amount of hysteresis in the insulating film. In one such embodiment, the damage may be caused by processing of the insulating film performed after formation of the insulating film.

An additional embodiment relates to a system that includes a measurement system and a computer-usable carrier medium. The measurement system is configured to measure an amount of hysteresis in an insulating film without contacting the insulating film. The carrier medium includes program instructions. The program instructions are executable on a computer system for determining the amount of hysteresis in the insulating film using measurements from the measurement system. Therefore, the system may be used to measure and determine electrical hysteresis properties of insulating films in a non-contact manner.

The measurement system may be configured as described above. An additional example of an appropriate measurement system is the Quantox or Quantox XP system, which is commercially available from KLA-Tencor. Further examples of appropriate measurement systems are illustrated in one or more of U.S. Pat. Nos. 5,594,247 to Verkuil et al., 5,767,693 to Verkuil, 5,834,941 to Verkuil, 6,060,709 to Verkuil et al., 6,072,320 to Verkuil, 6,091,257 to Verkuil et al., 6,097,196 to Verkuil et al., 6,104,206 to Verkuil, 6,121,783 to Homer et al., 6,191,605 to Miller et al., and 6,202,029 to Verkuil et al., which are incorporated by reference as if fully set forth herein. The measurement system may be configured as illustrated in any of these U.S. patents.

Program instructions implementing methods such as those described above may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

In an embodiment, the computer system may be configured to execute the program instructions to perform a computer-implemented method according to the above embodiments. The computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium. The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

It will be appreciated to those skilled in the art having the benefit of this disclosure that this invention is believed to provide methods and systems for non-contact hysteresis measurements of insulating films. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A non-contact method for determining a property of an insulating film, comprising:
    measuring an amount of hysteresis in the insulating film without contacting the insulating film; and
    determining the amount of hysteresis in the insulating film.

2. The method of claim 1, further comprising monitoring a presence of voids in the insulating film using the amount of hysteresis, wherein the amount of hysteresis is responsive to the presence of voids.

3. The method of claim 2, wherein the insulating film comprises a low-k insulating film.

4. The method of claim 2, wherein the insulating film comprises a high-k insulating film.

5. The method of claim 1, further comprising monitoring a presence of traps in the insulating film using the amount of hysteresis, wherein the amount of hysteresis is responsive to the presence of traps.

6. The method of claim 5, wherein the insulating film comprises a thermally grown film.

7. The method of claim 5, wherein the insulating film comprises a high-k insulating film.

8. The method of claim 1, wherein the insulating film comprises a thermally grown film, the method further comprising processing the thermally grown film prior to said measuring, and wherein the amount of hysteresis is responsive to traps in the thermally grown film caused by said processing.

9. The method of claim 1, further comprising processing the insulating film after formation of the insulating film and prior to said measuring, wherein the amount of hysteresis is responsive to damage of the insulating film caused by said processing.

10. The method of claim 9, wherein said processing comprises a plasma process.

11. The method of claim 1, wherein said measuring comprises measuring an electrical characteristic of the insulating film before and after applying an electrical field to the insulating film for a period of time.

12. The method of claim 1, wherein said measuring comprises stressing the insulating film by applying an electrical field to the insulating film, by heating the insulating film, or by applying ultraviolet light to the insulating film.

13. The method of claim 12, wherein said measuring further comprises measuring an electrical characteristic of the insulating film before and after said stressing.

14. The method of claim 1, further comprising measuring one or more other properties of the insulating film and determining the one or more other properties of the insulating film.

15. The method of claim 1, wherein the insulating film comprises an oxide, the method further comprising measuring trace metals in the oxide and determining an amount of the trace metals in the oxide.

16. A computer-implemented method for data analysis, comprising determining a single numeric value representing an amount of hysteresis in an insulating film from electrical characteristics of the insulating film, wherein the electrical characteristics are measured without contacting the insulating film.

17. The method of claim 16, wherein the electrical characteristics of the insulating film are measured before and after application of an electrical field to the insulating film, and wherein the electrical field is applied to the insulating film without contacting the insulating film.

18. The method of claim 16, further comprising analyzing a bulk charge trap density in the insulating film using the single numeric value.

19. The method of claim 16, further comprising analyzing polarization effects of voids in the insulating film using the single numeric value.

20. The method of claim 16, further comprising analyzing damage of the insulating film using the single numeric value, wherein the damage is caused by processing of the insulating film performed after formation of the insulating film.

21. A system, comprising:
  a measurement system configured to measure an amount of hysteresis in an insulating film without contacting the insulating film; and
  a computer-usable carrier medium comprising program instructions, wherein the program instructions are executable on a computer system for determining the amount of hysteresis in the insulating film using measurements from the measurement system.

* * * * *